United States Patent
Couderc et al.

(10) Patent No.: US 7,912,535 B2
(45) Date of Patent: Mar. 22, 2011

(54) METHOD AND SYSTEM FOR ASSESSING REPOLARIZATION ABNORMALITIES

(75) Inventors: Jean-Philippe Couderc, Rochester, NY (US); Martino Vaglio, Biella (IT)

(73) Assignee: University of Rochester, Rochester, NY (US)

( * ) Notice: Subject to any disclaimer, the term of this patent is extended or adjusted under 35 U.S.C. 154(b) by 688 days.

(21) Appl. No.: 11/680,896

(22) Filed: Mar. 1, 2007

(65) Prior Publication Data

US 2007/0208265 A1 Sep. 6, 2007

Related U.S. Application Data

(60) Provisional application No. 60/778,088, filed on Mar. 2, 2006.

(51) Int. Cl.
*A61B 5/04* (2006.01)

(52) U.S. Cl. ...................................................... 600/509

(58) Field of Classification Search .................. 600/512, 600/510, 509
See application file for complete search history.

(56) References Cited

U.S. PATENT DOCUMENTS

| 5,967,995 A | 10/1999 | Shusterman et al. |
| 6,438,409 B1 * | 8/2002 | Malik et al. .................... 600/512 |
| 2005/0234357 A1 | 10/2005 | Xue et al. |

OTHER PUBLICATIONS

Vaglio et al. "Fractionated Repolarization Induced by Sotalol in Healthy Subjects." Computers in Cardiology Dec. 1, 2005; 32:523-526.*

Vaglio, M., Couderc, JP., Xia, X., Zareba, W., "Fractionated Repolarization Induced by Sotalol in Healthy Subjects." Computers in Cardiology 2005; 32:523-526.

Vaglio et al., "Fractionated Repolarization Induced by Sotalol in Healthy Subjects," Computers in Cardiology 32:523-526 (2005).

* cited by examiner

*Primary Examiner* — George Manuel
*Assistant Examiner* — Robert N Wieland
(74) *Attorney, Agent, or Firm* — Robert D. Gunderman, Jr.; Patent Technologies, LLC

(57) ABSTRACT

A method for assessing repolarization abnormalities is disclosed. At least two repolarization signals are identified from a set of ECG signals. PCA analysis is performed on the at least two repolarization signals to extract at least eigenvectors $ev_1$ and $ev_2$. A maximum vector MV is determined based on a transformed ECG signal in a plane defined by $ev_1$ and $ev_2$. A repolarization duration is determined which is based on the maximum vector MV. A system for assessing repolarization abnormalities is also disclosed. The system has a processor configured to determine a repolarization duration which is based on a maximum vector MV from transformed ECG repolarization signals in a plane defined by eigenvectors $ev_1$ and $ev_2$ which result from PCA analysis on the ECG repolarization signals. The system also has a data input coupled to the processor and a user interface coupled to either the processor or the data input.

75 Claims, 10 Drawing Sheets

METHOD AND SYSTEM FOR ASSESSING REPOLARIZATION ABNORMALITIES

RELATED APPLICATIONS

This patent application claims priority to provisional U.S. patent application 60/778,088, entitled "Assessment of Repolarization Abnormalities from an Electrocardiographic Signal", filed Mar. 2, 2006. Provisional U.S. patent application 60/778,088 is hereby officially incorporated by reference in its entirety.

FIELD

The claimed invention relates to the assessment of repolarization abnormalities of the heart, and more particularly to a methods and systems which assess repolarization abnormalities based on determination of one or more repolarization durations based in part on a threshold percentage of a maximum heart vector.

BACKGROUND

The electrocardiogram (ECG) is based on the electrical activity of the heart muscle cells. In the resting stage, the inside of the cardiac cells has a negative charge compared to the outside of the cells. The resulting voltage difference between the internal and the external spaces of the cell membrane is called transmembrane potential. The discharging of this voltage is known as depolarization and is associated with the start of the contraction of the heart muscle cell fibers. After contraction of the ventricles, the heart muscle cells redevelop substantially the same voltage over the cell membrane. This recovery phase is called the repolarization process of the heart ventricles. An ECG measured from the skin surface measures a total electrical component created by the depolarization and repolarization of the heart's muscular cells.

The repolarization of the heart is made possible in part by ion channels within the myocardial cells of the heart which allow an ion current to redistribute charge. It is highly important that the regulation of the ion currents during the ventricular repolarization process occurs without interference, since a delay in this process or any other abnormalities can lead to a substantially increased risk for sudden cardiac death.

Recently, several important drugs have been removed from the market after it was revealed that these drugs were causing repolarization abnormalities in certain patients. It was determined that these repolarization abnormalities were induced by pharmacological compounds reducing the rapidly activating delayed rectifier potassium current ($I_{Kr}$) of the myocardial cells. The undesirable effect of these repolarization abnormalities was not fully identified in the existing safety assessment studies, which were mainly interested on a time interval which was not necessarily indicative of a change in repolarization morphology. The U.S. Food and Drug Agency (FDA) currently recommends that all pharmaceutical companies test the safety of all new compounds for their potential QT prolonging effect. The QT interval of an ECG encompasses a portion of the repolarization interval. Unfortunately, there is no standard for the measurement of a QT interval, and various techniques used to measure QT interval are not sensitive enough to properly identify a drug associated with a very small yet potentially deadly prolongation of the QT interval. Furthermore, as previously mentioned, QT interval does not quantify changes in the morphology (which includes both amplitude and duration) of the repolarization interval. Consequently, there is a need for other electrocardiographic markers besides QT prolongation for the identification of repolarization abnormalities.

SUMMARY

A method for assessing repolarization abnormalities is disclosed. At least two repolarization signals (at least one repolarization signal from a first location and at least a second repolarization signal from a second location) are identified from a set of electrocardiogram (ECG) signals. Principal component analysis is performed on the at least two repolarization signals to extract at least eigenvectors $ev_1$ and $ev_2$. A maximum vector MV is determined based on a transformed ECG signal in a plane defined by $ev_1$ and $ev_2$. A repolarization duration is determined which is based on the maximum vector MV.

A computer readable medium having stored thereon instructions for assessing repolarization abnormalities, which, when executed by a processor, causes the processor to perform the steps according to the previous method is disclosed.

A system for assessing repolarization abnormalities is disclosed. The system has a processor configured to determine a repolarization duration which is based on a maximum vector MV from transformed ECG repolarization signals in a plane defined by eigenvectors $ev_1$ and $ev_2$ which result from principal component analysis on the ECG repolarization signals. The system also has a data input coupled to the processor and configured to provide the processor with the ECG data. The system further has a user interface coupled to either the processor or the data input.

A data signal for transmission over a transmission medium is disclosed. The data signal includes a repolarization duration selected from the group consisting of early repolarization duration (ERD), late repolarization duration (LRD), and total repolarization duration (TRD).

A method for analyzing an effect of a pharmacological agent on heart repolarization is also disclosed. A first set of ECG signals is obtained. At least two repolarization signals are identified from the first set of ECG signals. Principal component analysis is performed on the at least two repolarization signals from the first set of ECG signals to extract at least first eigenvectors $ev_{1-1}$ and $ev_{1-2}$. A first maximum vector $MV_1$ is determined based on a first transformed ECG signal in a first plane defined by $ev_{1-1}$ and $ev_{1-2}$. A first repolarization duration is determined which is based on the first maximum vector $MV_1$. The pharmacological agent is administered. A second set of ECG signals is obtained. At least two repolarization signals are identified from the second set of ECG signals. Principal component analysis is performed on the at least two repolarization signals from the second set of ECG signals to extract at least second eigenvectors $ev_{2-1}$ and $ev_{2-2}$. A second maximum vector $MV_2$ is determined based on a second transformed ECG signal in a second plane defined by $ev_{2-1}$ and $ev_{2-2}$. A second repolarization duration is determined which is based on the second maximum vector $MV_2$. A repolarization abnormality is detected based on the first repolarization duration and the second repolarization duration.

It is at least one goal of the claimed invention to provide an improved electrocardiographic marker besides QT prolongation for the identification of repolarization abnormalities.

Figure 1:
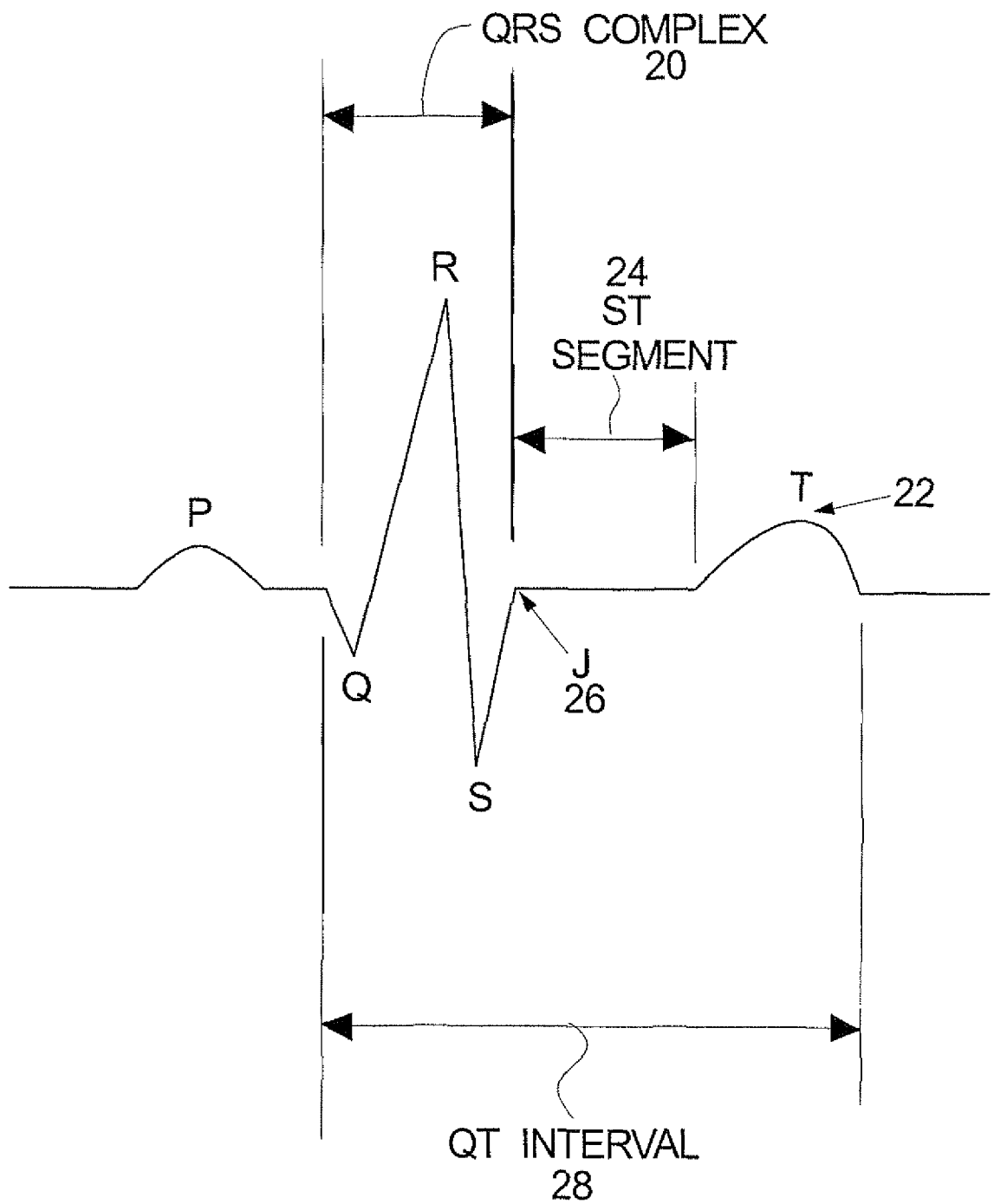
FIG. 1 schematically illustrates an ECG signal over one heart beat.

It will be appreciated that for purposes of clarity and where deemed appropriate, reference numerals have been repeated in the figures to indicate corresponding features, and that the various elements in the drawings have not necessarily been drawn to scale in order to better show the features.

DETAILED DESCRIPTION

A surface electrocardiogram (ECG) may be measured by an ECG capture device which can have one or more leads which are coupled to a person's body in various locations. The electrical activity occurring within individual cells throughout the heart produces a cardiac electrical vector which can be measured at the skin's surface by the ECG capture device leads. The signal registered at the skin's surface originates from many simultaneously propagating activation fronts at different locations, each of which affects the size of the total component. One type of ECG capture device is a twelve-lead signal device, although ECG capture devices of any number of leads may be used to gather a set of ECG signals for use in assessing repolarization abnormality.

FIG. 1 schematically illustrates an embodiment of an ECG showing one heart beat and some of the labels which are commonly assigned to various portions of the ECG signal. The QRS complex 20 is associated with the depolarization of the heart ventricles. The QT interval 28 and the T-wave 22 are associated with repolarization of the heart ventricles. The ST segment 24 falls between the QRS complex 20 and the T-wave 22. The J point 26 is located where the QRS complex 20 joins the ST segment 24. For reference, the QT interval 28 discussed above and used in pre-existing FDA drug testing is illustrated. Unfortunately, QT interval 28 has been shown to be a less reliable and less precise measurement of repolarization abnormalities than desired, and therefore a better method is needed.

Figure 2:
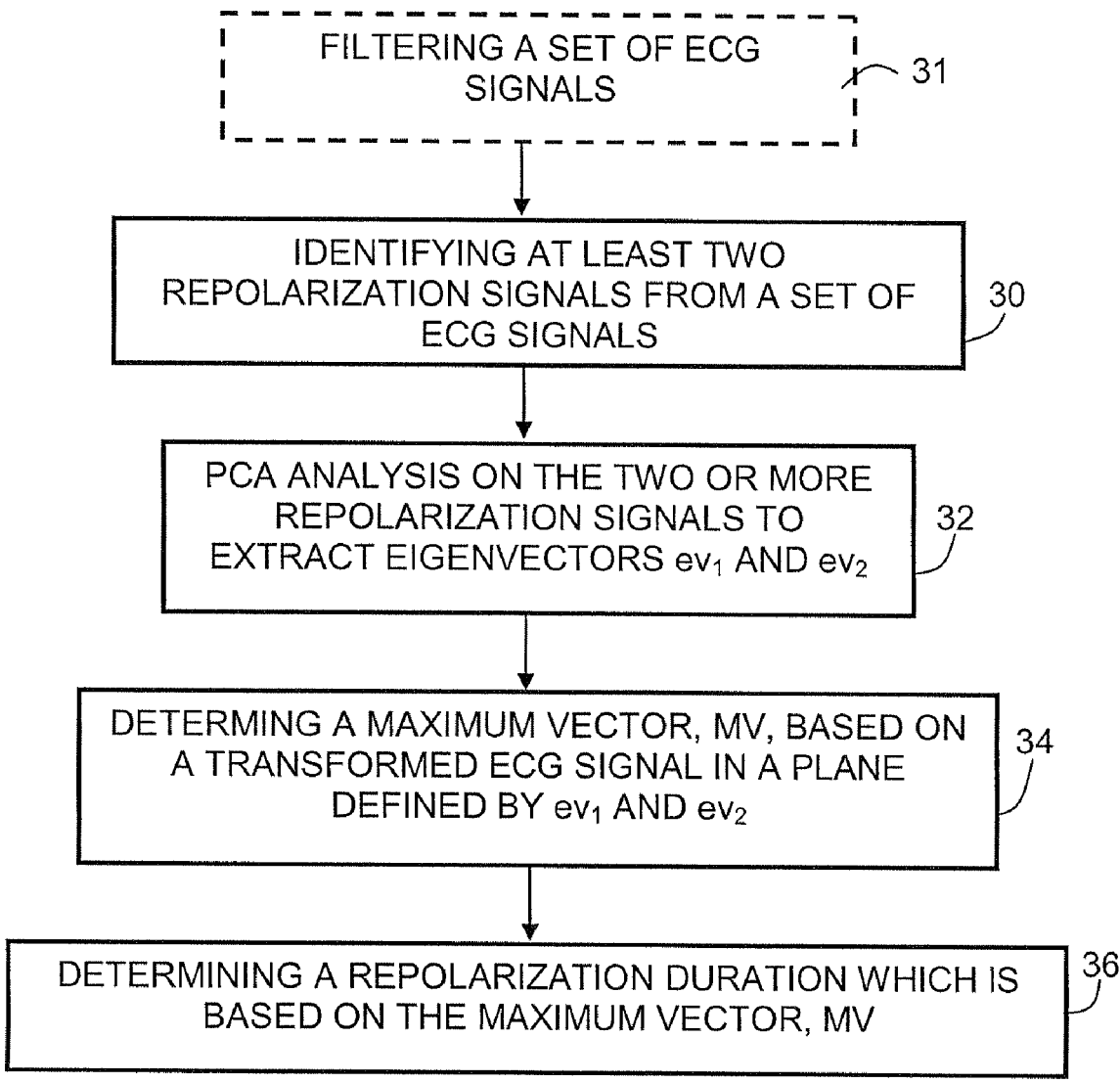
FIG. 2 illustrates one embodiment of a method for assessing repolarization abnormalities.

FIG. 2 illustrates one embodiment of a such a method for assessing repolarization abnormalities. At least two repolarization signals are identified 30 from a set of ECG signals. The ECG signals may be obtained from a variety of ECG capture devices as discussed above. The ECG signals may be obtained in "real-time" from a subject, or the ECG signals may be obtained from a database (which should be understood to include memory devices) storing previously obtained ECG signals.

Each repolarization signal generally includes the T-wave 22, and there are various ways to identify 30 the repolarization signals. The repolarization signals can be identified 30 using a match template filter. Alternatively, each repolarization signal can be identified 30 as starting from the J point 26 and ending at a point relative to a following R-peak. For example, the repolarization signal could be defined as starting from point J 26 and ending at a point 220 milliseconds prior to the following R-peak. Other embodiments could use other times prior to the following R-peak besides 220 milliseconds. Some methods to identify 30 or define the repolarization signals may include QRS complex detection, although this is not strictly necessary.

Although a minimum of two repolarization signals are needed for the analysis, it is preferable to have more than two signals. One example of a suitable number of repolarization signals is twelve signals, but fewer or more signals could be used in other embodiments. The identification of the repolarization signals from other ECG leads may be accomplished using the techniques described above or by using the time location(s) of repolarization intervals from a first ECG lead to identify the corresponding repolarization intervals from other ECG leads.

Prior to identifying 30 the at least two repolarization signals from a set of ECG signals, it may be necessary in some embodiments to filter 31 the set of ECG signals. Some sources of ECG data may already be filtered, however, in which case this step would not be necessary. In cases where the ECG data is not pre-filtered, filtering 31 of the ECG signals is recommended to remove baseline wander in the signals. One suitable method of filtering the ECG signals to remove baseline wander is digital low-pass FIR filtering. Another suitable method of filtering the ECG signals to remove baseline wander is to subtract a baseline estimation arrived-at using spline interpolation.

In other embodiments, the filtering 31 may include statistical combinations of multiple beats from the ECG signals. As a non-limiting example, a median beat may be created from a number of consecutive beats from each lead. In some embodiments, one or more leading beats may be discarded. In other embodiments, one or more trailing beats may be discarded. In further embodiments, only beats with a stable heart rate may be taken into account. An example of a suitable definition of beats with a stable heart rate is when the heart rate for a given beat varies less than ten percent in beats of the previous two minutes. In other embodiments other percentages, timeframes, and definitions of a stable heart rate may be used without deviating from the scope of the claimed invention.

Once the at least two repolarization signals are identified 30, principal component analysis 32 can be done on the repolarization signals to extract eigenvectors $ev_1$ and $ev_2$. Principal component analysis (PCA) is a way of identifying patterns in data, and is especially useful in dealing with multi-dimensional data, such as multiple repolarization signals from multiple ECG leads. PCA analysis is a mathematical technique which those skilled in the art will be familiar with, and results in a matrix of eigenvectors. As a summary of the PCA analysis, first, the mean is subtracted from each of the data dimensions. This produces a data set whose mean is zero. Next, a covariance matrix is calculated for the data. If the data has n-dimensions, then the covariance matrix will be a square n-by-n matrix. Mathematical constructs called eigenvectors and eigenvalues may be calculated for a square matrix, and so next, a set of eigenvectors and eigenvalues are calculated for the covariance matrix. For the n-by-n covariance matrix, there will be n eigenvectors. The eigenvectors are orthogonal to each other, and each has a corresponding eigenvalue. The eigenvectors can be thought of as a representation of the multi-dimension data. The eigenvector with the highest eigenvalue is the principal component of the data set. The eigenvectors may be sorted from highest to lowest, and the eigenvectors with the two highest eigenvalues may be referred to as $ev_1$ and $ev_2$ respectively.

Once the PCA analysis 32 has been completed, a maximum vector MV may be determined 34 based on a transformed ECG signal in a preferential plane defined by $ev_1$ and $ev_2$. Mathematically, MV is detected at time $t=T_{MV}$, where equation 1 is fulfilled:

$$MV = \max \langle \overrightarrow{VECG}(t) - \overrightarrow{VECG}(T_Q) \rangle, \quad \text{Equation 1}$$

where $\overrightarrow{VECG}(t) = \overrightarrow{ev}_1(t) + \overrightarrow{ev}_2(t)$, and $T_Q$ is the time coinciding with the beginning of the QRS complex. So, in conclusion, Equation 1 can be rewritten as:

$$MV = \max \sqrt{\{ev_1(t) - ev_1(T_Q)\}^2 + \{ev_2(t) - ev_2(T_Q)\}^2},$$

and $t=T_{MV}$ is defined as the value for t where Equation 1 is fulfilled.

Figure 3:
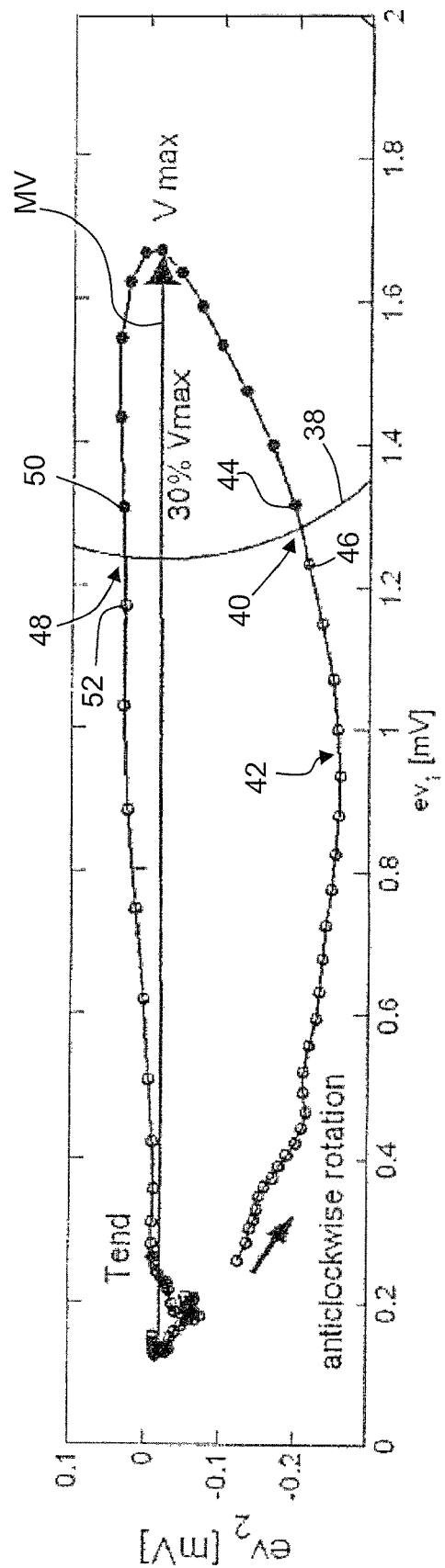
FIG. 3 illustrates one example of an embodiment of a T-loop plotted in a preferential plane.

Although not necessary to the determination 34 of the maximum vector MV, a graphical representation of MV in the plane defined by $ev_1$ and $ev_2$ is illustrated in FIG. 3 and labeled Vmax.

Referring again to FIG. 2, once the maximum vector MV has been determined, a repolarization duration which is based on the maximum vector MV is determined 36. The repolarization duration may be determined 36 by taking an arbitrary threshold percentage of the magnitude of MV and projecting the threshold magnitude relative to an endpoint of MV to determine a beginning point and an ending point on the transformed ECG signal in the plane defined by $ev_1$ and $ev_2$. An example of this process can be seen graphically in FIG. 3. In the example of FIG. 3, the arbitrary threshold percentage of the magnitude of MV is 30%. This threshold magnitude of 30% MV (or 30% Vmax) is projected in a circle or arc 38 around the endpoint of MV, which is labeled Vmax. Where the projected threshold 38 crosses 40 the transformed ECG signal 42 (or T-loop) on a first side of the endpoint of MV, we can define a beginning point. Since the data points are samples in time, the beginning point may be designated as the closest true data point 44 to the crossing point 40. Alternatively, the beginning point may be an interpolated data point based on the two closest data points 44 and 46. Where the projected threshold 38 crosses 48 the transformed ECG signal 42 (or T-loop) on a second side of the endpoint of MV, we can define an ending point. Since the data points are samples in time, the ending point may be designated as the closest true data point 50 to the crossing point 48. Alternatively, the ending point may be an interpolated data point based on the two closest data points 50 and 52.

Repolarization durations may be defined in three different ways: As an early repolarization duration (ERD), as a late repolarization duration (LRD), and/or as a total repolarization duration (TRD).

1) Early Repolarization Duration ($ERD_{x\%}$) can be defined as follows:

$ERD_{x\%} = T_{MV} - T_E$, where $T_E$ is the value for t where Equation 2 is fulfilled:

$$\|VECG(t) - VECG(T_{MV})\| = MV \cdot x\%, \text{ with } t < T_{MV} \quad \text{Equation 2}$$

Figure 4A:
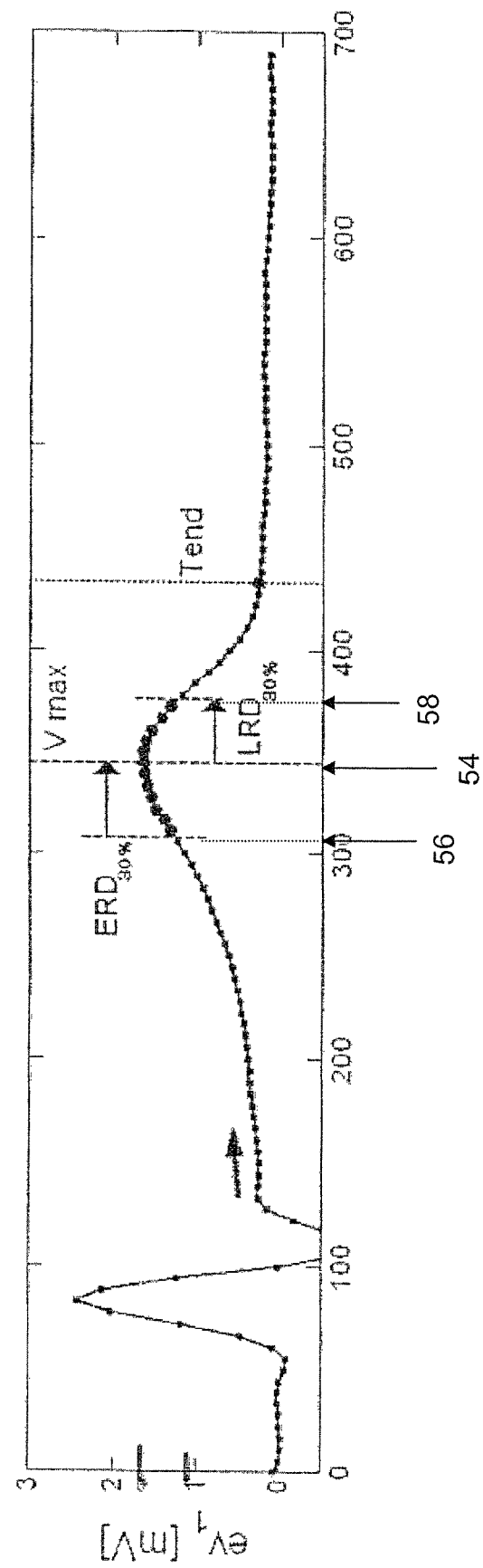
FIGS. 4A and 4B illustrate examples of primary and secondary components of an ECG signal plotted versus time.
Figure 4B:
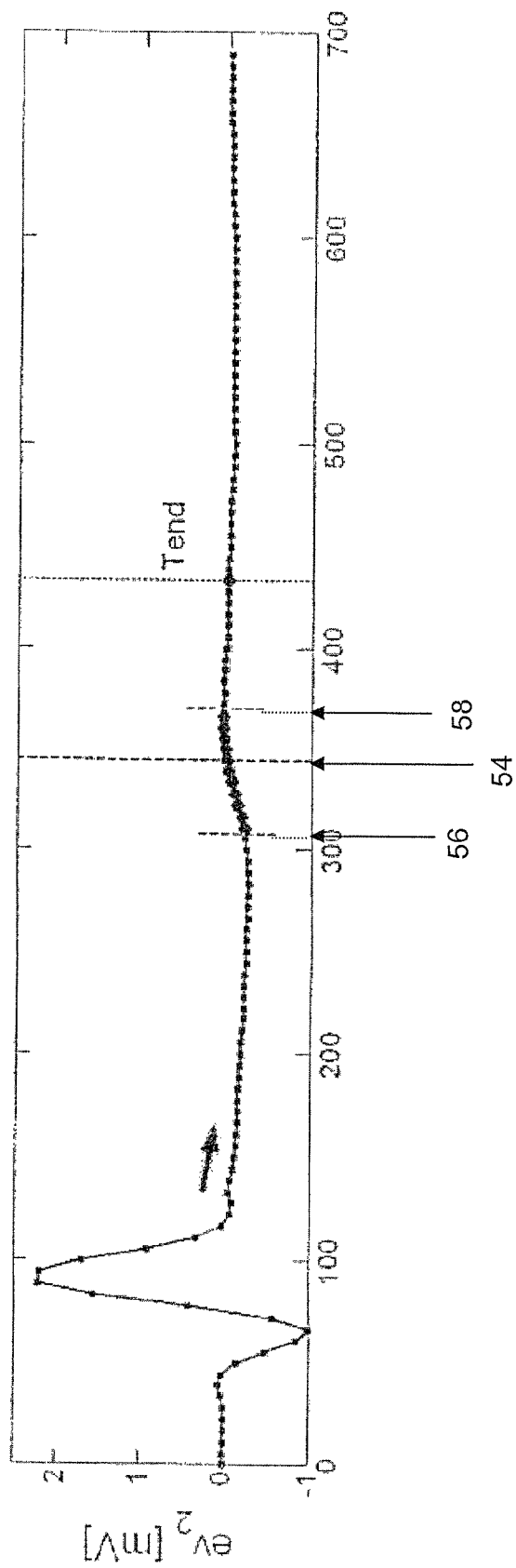

The determination of $ERD_{x\%}$ may also be seen graphically in FIGS. 3, 4A, and 4B. In the example of FIGS. 3, 4A, and 4B, the threshold percentage is 30%, so the parameter being determined in this example is $ERD_{30\%}$. It should be understood, however, that other threshold percentages may be used in other embodiments. A peak time corresponds to the endpoint of MV in FIG. 3. The term "peak" does not necessarily refer to a peak voltage in a plot of voltage versus time. Instead, the work "peak" refers to the occurrence of the maximum heart vector. A beginning time corresponds to the beginning point 40 or 44 as discussed above, depending on whether an exact or interpolated data point is used. The $ERD_{30\%}$ is the time difference between the peak time and the beginning time. The time values corresponding to the peak time 54 and the beginning time 56 are shown in FIGS. 4A and 4B, which are a plot of the primary component $ev_1$ signal data over time and a plot of the secondary component $ev_2$ signal data over time, respectively. The time axis may be expressed in actual time units or in samples per second which can easily be converted to time with a knowledge of the sampling rate. $ERD_{30\%}$ is illustrated in FIGS. 4A and 4B as the difference between the peak time 54 and the beginning time 56, the beginning time being determined by the threshold percentage as described above. Although both the $ev_1$ plot of FIG. 4A and the $ev_2$ plot of FIG. 4B are illustrated, only one ev plot needs to be generated if a graphical method is used to determine a repolarization duration.

2) Late Repolarization Duration ($LRD_{x\%}$) can be defined as follows:

$LRD_{x\%} = T_L - T_{MV}$, where $T_L$ is the value for t where equation 3 is fulfilled:

$$\|VECG(t) - VECG(T_{MV})\| = MV \cdot x\%, \text{ with } t > T_{MV} \quad \text{Equation 3}$$

The determination of $LRD_{x\%}$ may also be seen graphically in FIGS. 3, 4A, and 4B. In the example of FIGS. 3, 4A, and 4B, the threshold percentage is 30%, so the parameter being determined in this example is $LRD_{30\%}$. It should be understood, however, that other threshold percentages may be used in other embodiments. A peak time corresponds to the endpoint of MV in FIG. 3. An ending time corresponds to the ending point 48 or 50 as discussed above, depending on whether an exact or interpolated data point is used. The $LRD_{30\%}$ is the time difference between the ending time and the peak time. The time values corresponding to the peak time 54 and the ending time 58 are shown in FIGS. 4A and 4B. $LRD_{30\%}$ is illustrated in FIGS. 4A and 4B as the difference between the ending time 58 and the peak time 54, the ending time being determined by the threshold percentage as described above.

3) Total Repolarization Duration ($TRD_{x\%}$), can be defined as the sum of $ERD_{x\%}$ and $LRD_{x\%}$. It should be noted that ERD, LRD, and TRD may be calculated for an infinite variety of percentages. A change in ERD, LRD, and/or TRD at a given threshold percentage x % has been shown to be indicative of a repolarization abnormality, as will be discussed in greater detail later in this specification. It should also be noted that ERD and LRD may be determined at the same threshold percentages or at different threshold percentages. Similarly, TRD may be determined by adding an ERD and LRD value determined based on the same threshold percentage, or TRD may be determined by adding an ERD and LRD value determined based on different threshold percentages.

The ERD, LRD, and TRD parameters may be advantageously used to quantify abnormalities of the electrocardiographic signals induced by pharmacological compounds reducing various ion kinetics including the rapidly activating delayed rectifier potassium current of the myocardial cells ($I_{Kr}$). The ERD, LRD, and TRD markers can assist in identifying abnormal electrophysiological phenomenon associated with drug cardiotoxicity. The ERD, LRD, and TRD markers are interval duration measurements (which correlate to changes in morphology of the repolarization interval) realized inside a specific portion of the electro- and vecto-cardiographic signal recorded on or from within the human body (in the case of an implantable or partially implantable device). Based on the principal component analysis of the ECG signal, specific intervals of the vectocardiographic representation of the repolarization loop are determined when projected in its preferential plane. Based on a two-dimension geometric threshold applied to the maximum vector magnitude of the vectocardiographic representation of the repolarization process, an interval is delimited. The point around which the two-dimension threshold is applied is the time point where the vectocardiographic vector is the largest. The duration of the early, late, and/or total part of this interval may be determined. The determination of ERD, LRD, and/or TRD may be done for each cardiac beat or the determination can be made for median cardiac cycles.

Figure 5:
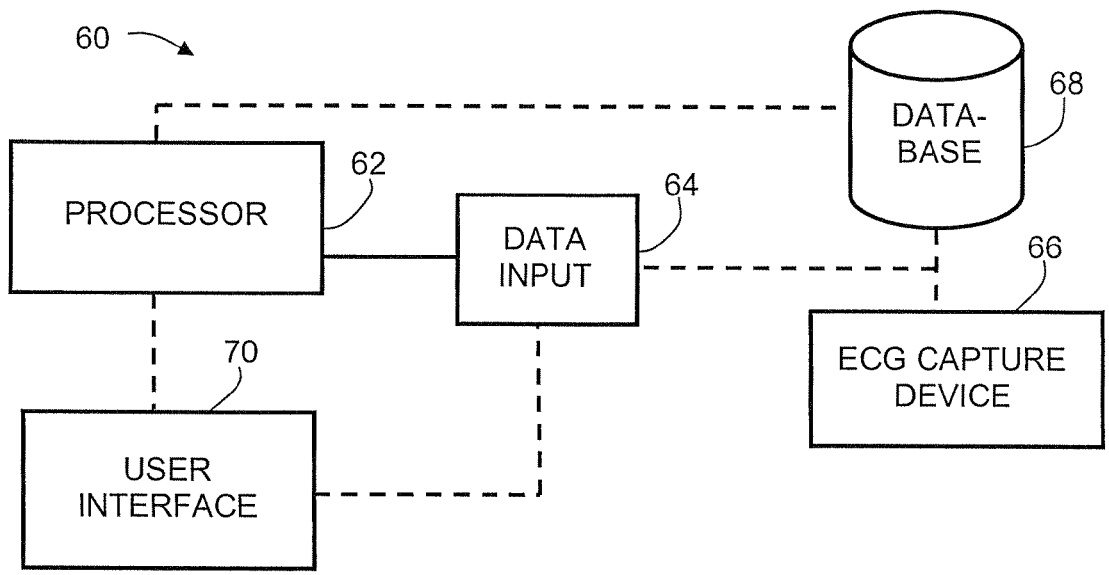
FIG. 5 schematically illustrates one embodiment of a system for assessing repolarization abnormalities.

FIG. 5 schematically illustrates an embodiment of a system 60 for assessing repolarization abnormalities. The system has a processor 62 which is configured to determine a repolarization duration which is based on a maximum vector MV from transformed ECG repolarization signals in a plane defined by eigenvectors $ev_1$ and $ev_2$ which result from principal component analysis on the ECG repolarization signals. Embodiments of suitable processes and method steps to make the determination of MV have already been discussed above. The processor 62 may be a computer executing machine readable instructions which are stored on a CD, a magnetic tape, an optical drive, a DVD, a hard drive, a flash drive, a memory card, a memory chip, or any other computer readable medium. The processor 62 may alternatively or additionally include a laptop, a microprocessor, an application specific integrated circuit (ASIC), digital components, electrical components, or any combination thereof. The processor 62 may be a stand-alone unit, or it may be a distributed set of devices.

A data input 64 is coupled to the processor 62 and configured to provide the processor with ECG data. An ECG capture device 66 may optionally be coupled to the data input 64 to enable the live capture of ECG data. Examples of ECG capture devices include, but are not limited to, a twelve-lead ECG device, an eight-lead ECG device, a two lead ECG device, a Holter device, a bipolar ECG device, and a uni-polar ECG device. Similarly, a database 68 may optionally be coupled to the data input 64 to provide previously captured ECG signal data to the processor. Database 68 can be as simple as a memory device holding raw data or formatted files, or database 68 can be a complex relational database. Depending on the embodiment, none, one, or multiple databases 68 and/or ECG capture devices 66 may be coupled to the data input 64. The ECG capture device 66 may be coupled to the data input 64 by a wired connection, an optical connection, or by a wireless connection. Suitable examples of wireless connections may include, but are not limited to, RF connections using an 802.11x protocol or the Bluetooth® protocol. The ECG capture device 66 may be configured to transmit data to the data input 64 only during times which do not interfere with data measurement times of the ECG capture device 66. If interference between wireless transmission and the measurements being taken is not an issue, then transmission can occur at any desired time. Furthermore, in embodiments having a database 68, the processor 62 may be coupled to the database 68 for storing results or accessing data by bypassing the data input 64.

The system 60 also has a user interface 70 which may be coupled to either the processor 62 and/or the data input 64. The user interface 70 can be configured to display the ECG signal data, the T-loop plotted in the preferential plane as discussed above, and/or calculated parameters such as ERD, LRD, and TRD at one or more threshold percentages. The user interface 70 may also be configured to allow a user to select ECG signals from a database 68 coupled to the data input 64, or to start and stop collecting data from an ECG capture device 66 which is coupled to the data input 64.

Figure 6:
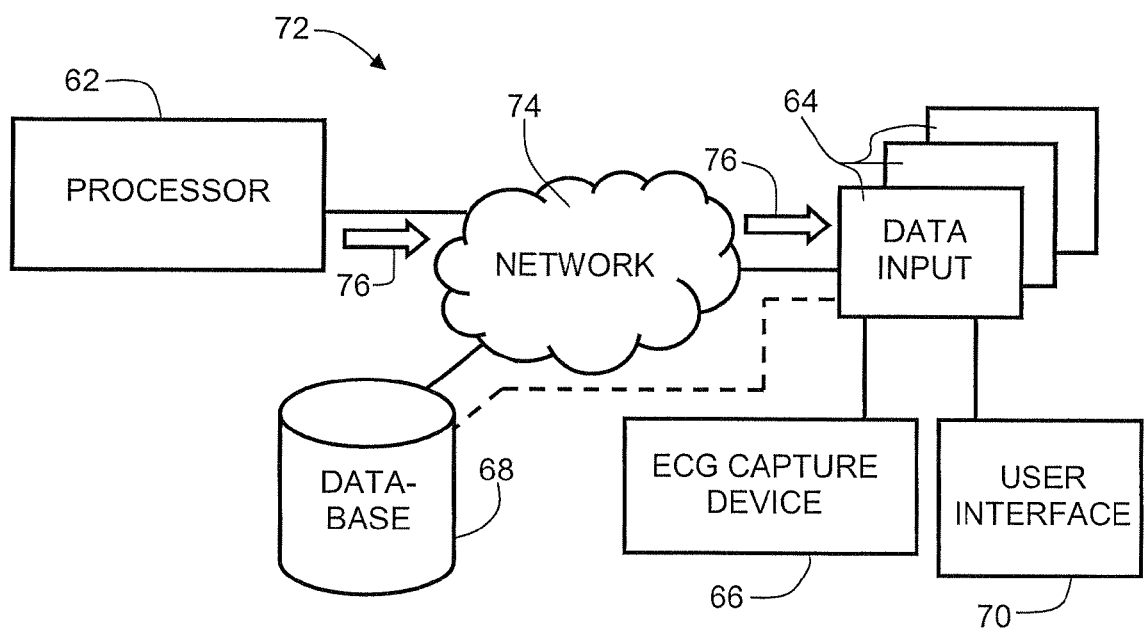
FIG. 6 schematically illustrates another embodiment of a system for assessing repolarization abnormalities.

FIG. 6 schematically illustrates another embodiment of a system 72 for assessing repolarization abnormalities. In this embodiment, the processor 62 is set-up to be a remote processor which is coupled to the data input 64 over a network 74. The network 74 may be a wired or wireless local area network (LAN or WLAN) or the network 74 may be a wired or wireless wide area network (WAN, WWAN) using any number of communications protocols to pass data back and forth. Having a system 72 where the processor 62 is located remotely allows multiple client side data inputs 64 to share the resources of the processor 62. ECG signals may be obtained by the data input 64 from a database 68 and/or an ECG capture device 66 under the control of a user interface 70 coupled to the data input 64. The ECG signal data may then be transferred over the network 74 to the processor 62 which can then determine one or more repolarization duration parameters ERD, LRD, and TRD for one or more threshold percentages and transmit data signals 76 having one or more of the ERD, LRD, and/or TRD parameters to the client side. Such data transmissions may take place over a variety of transmission media, such as wired cable, optical cable, and air. In this embodiment, the remote processor 62 can be used to help keep the cost of the client-side hardware down, and can facilitate any upgrades to the processor or the instructions being carried out by the processor, since there is a central upgrade point.

Figure 7:
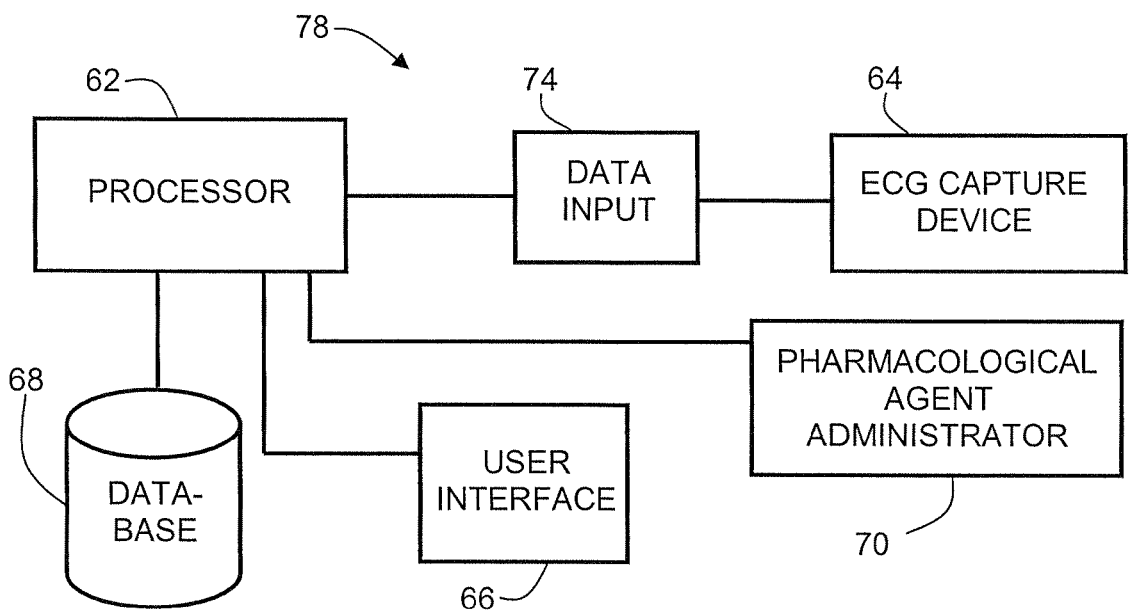
FIG. 7 schematically illustrates a further embodiment of a system for assessing repolarization abnormalities.

FIG. 7 schematically illustrates a further embodiment of a system 78 for assessing repolarization abnormalities. In this embodiment, a data input 64, a user interface 70, and a database 68 are coupled to the processor 62. An ECG capture device 66 is coupled to the data input 64. The system 78 also has a pharmacological agent administrator 80 which is coupled to the processor 62. The pharmacological agent administrator 80 may be configured to administer a pharmacological agent to a patient when enabled by the processor 62. The system 78 of FIG. 7, and its equivalents, may be useful in automating the analysis of the effects of pharmacological agents on heart repolarization. Repolarization duration parameters ERD, LRD, and/or TRD may first be determined at one or more threshold percentages. Then, the processor can instruct the pharmacological agent administrator 80 to administer a pharmacological agent. Then, repolarization duration parameters ERD, LRD, and/or TRD may be determined a second time at one or more threshold percentages. Changes in the one or more repolarization duration parameters are indicative of a change in the T-wave morphology, since changes in both the amplitude and the duration of the repolarization interval will affect the repolarization duration parameters ERD, LRD and TRD. Different threshold percentages for which ERD, LRD, and TRD are determined may be more applicable than others for the screening of a particular pharmacological agent or heart condition. Therefore, although only one threshold percentage can be used in some embodiments, it will sometimes be recommended to determine ERD, LRD, and/or TRD at multiple threshold percentages.

Figure 8:
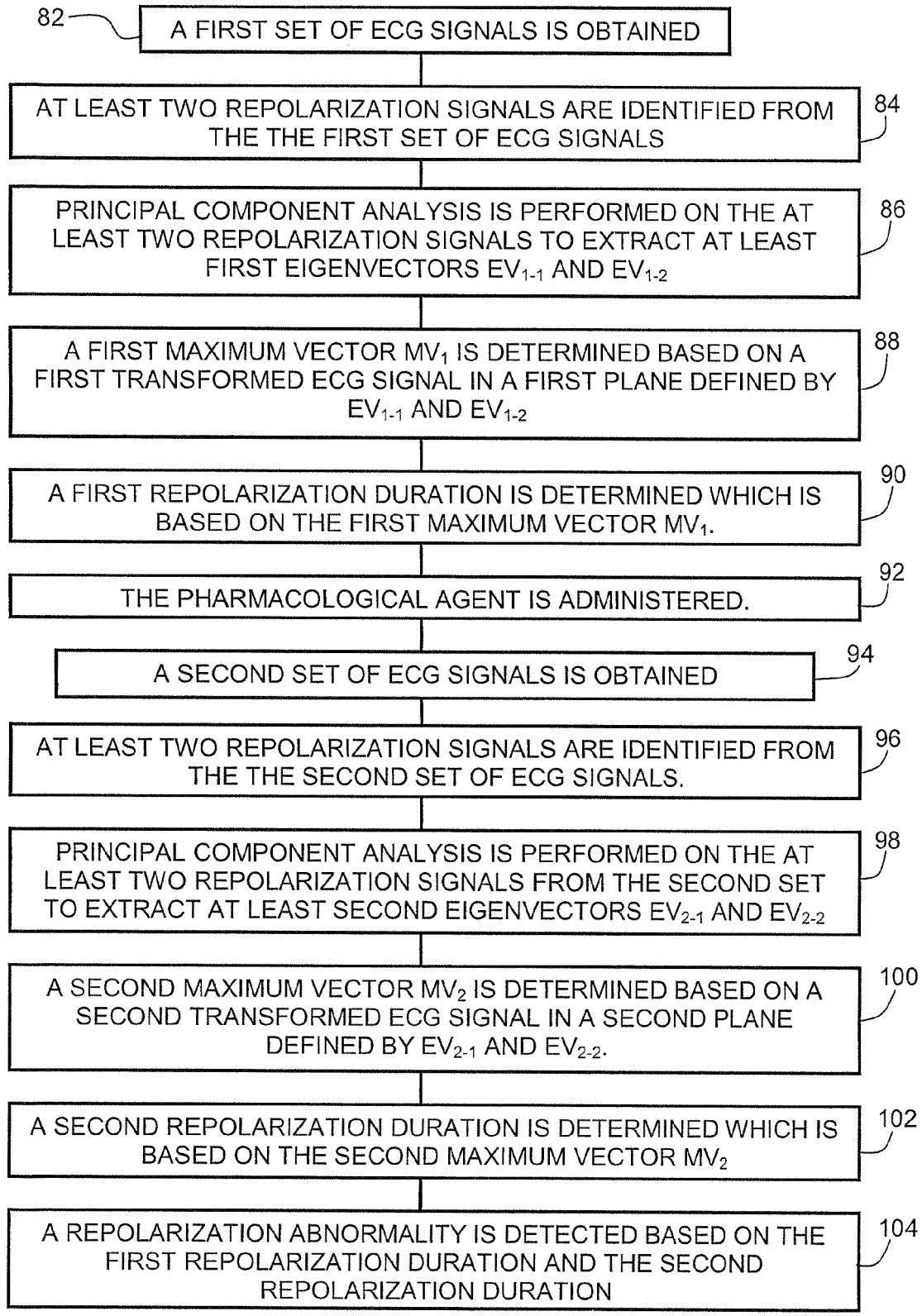
FIG. 8 illustrates one embodiment of a method for analyzing an effect of a pharmacological agent on heart repolarization.

FIG. 8 illustrates one embodiment of a method for analyzing an effect of a pharmacological agent on heart repolarization. A first set of ECG signals is obtained 82. At least two repolarization signals are identified 84 from the first set of ECG signals. Principal component analysis 86 is performed on the at least two repolarization signals to extract at least first eigenvectors $ev_{1-1}$ and $ev_{1-2}$. A first maximum vector $MV_1$ is determined 88 based on a first transformed ECG signal in a first plane defined by $ev_{1-1}$ and $ev_{1-2}$. A first repolarization duration is determined 90 which is based on the first maximum vector $MV_1$. The pharmacological agent is administered 92. A second set of ECG signals is obtained 94. At least two repolarization signals are identified 96 from the second set of ECG signals. Principal component analysis 98 is performed on the at least two repolarization signals from the second set to extract at least second eigenvectors $ev_{2-1}$ and $ev_{2-2}$. A second maximum vector $MV_2$ is determined 100 based on a second transformed ECG signal in a second plane defined by $ev_{2-1}$ and $ev_{2-2}$. A second repolarization duration is determined 102 which is based on the second maximum vector $MV_2$. A repolarization abnormality is detected 104 based on the first repolarization duration and the second repolarization duration. Suitable examples of repolarization durations include ERD, LRD, and/or TRD at one or more threshold percentages as discussed previously.

Figure 9:
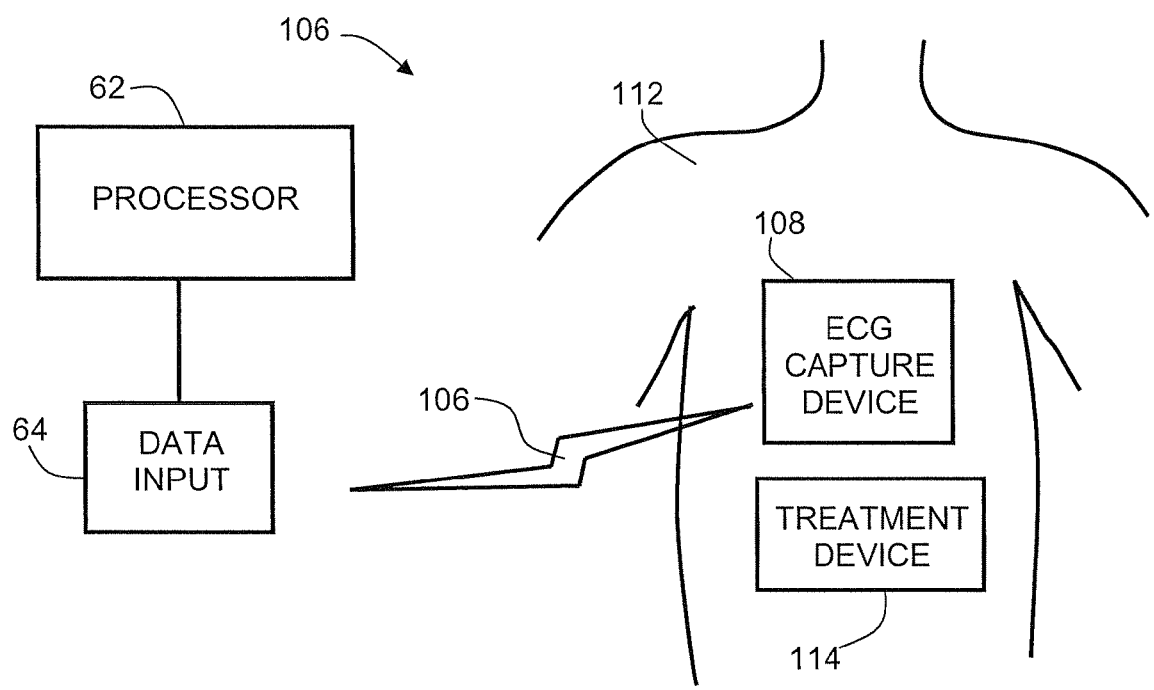
FIG. 9 schematically illustrates another embodiment of a system for assessing repolarization abnormalities.

FIG. 9 schematically illustrates another embodiment of a system 106 for assessing repolarization abnormalities. Similar to other embodiments, the system has a processor 62 which is coupled to a data input 64. An ECG capture device 108 is coupled 110 to the data input. The coupling 110 may be wired or wireless. The ECG capture device 108 is configured so that at least a portion of the ECG capture device 108 is implantable in a subject's body 112. The processor 62 and the data input 64 are external to the subject's body 112 in this embodiment, however, in other embodiments, the processor 62 and/or the data input 64 could be partially or entirely implanted in the subject's body 112. The system 106 of FIG. 9 may optionally have a treatment device 114 coupled to the processor 62. In this case, the processor 62 may be configured to activate the treatment device to attempt to correct a repolarization abnormality indicated by one or more repolarization duration parameters ERD, LRD, and TRD based on one or more threshold percentages. Suitable examples of treatment devices 114 include, but are not limited to a pharmacological agent administrator and a defibrillator. The treatment device 114 may also be partially or completely implanted inside of the subject 112.

Repolarization duration parameters, as discussed above, based on a vectorial model have been used in validations with encouraging results. Two studies have shown that such measurements are statistically increased in the cardiac signal of an individual exposed to a pharmacological agent reducing the $I_{Kr}$ currents.

First Validation:

An analysis realized on the data from a study involving sotalol, a drug modifying $I_{Kr}$ ion currents, revealed early changes of the repolarization loop prior to the identification of a prolongation of the interval QT as shown in Table 1.

TABLE 1

| Δ on drug - baseline | 42'-48' after dosing | 48'-54' after dosing | 54'-1 h after dosing | 1 h-1 h 6' after dosing |
|---|---|---|---|---|
| QTc L II (ms) | 4.0(16) | 4.1(16) | 4.3(16)* | 13(17)* |
| ERDc 50% (ms) | 5.1(14)* | 4.9(14)* | 4.4(12) | 9.5(16)** |

TABLE 1-continued

| Δ on drug - baseline | 42'-48' after dosing | 48'-54' after dosing | 54'-1 h after dosing | 1 h-1 h 6' after dosing |
|---|---|---|---|---|
| LRDc 50% (ms) | 1.1(6.2)* | 0.6(5.2)* | 0.3(6.5) | 4.0(5.9)** |

*$p < 0.05$,
**$p <= 0.002$, median value and their standard deviation between parenthesis.
ERD and LRD were corrected using individual correction formula based on 6-hour continuous data.

The analysis of the T-loop morphology provide new insight into $I_{Kr}$-related changes of the repolarization process induced by the drug sotalol known as an $I_{Kr}$ blocking agent. These changes are detected prior to a significant prolongation of the interval QT.

Second Validation

Figure 10:
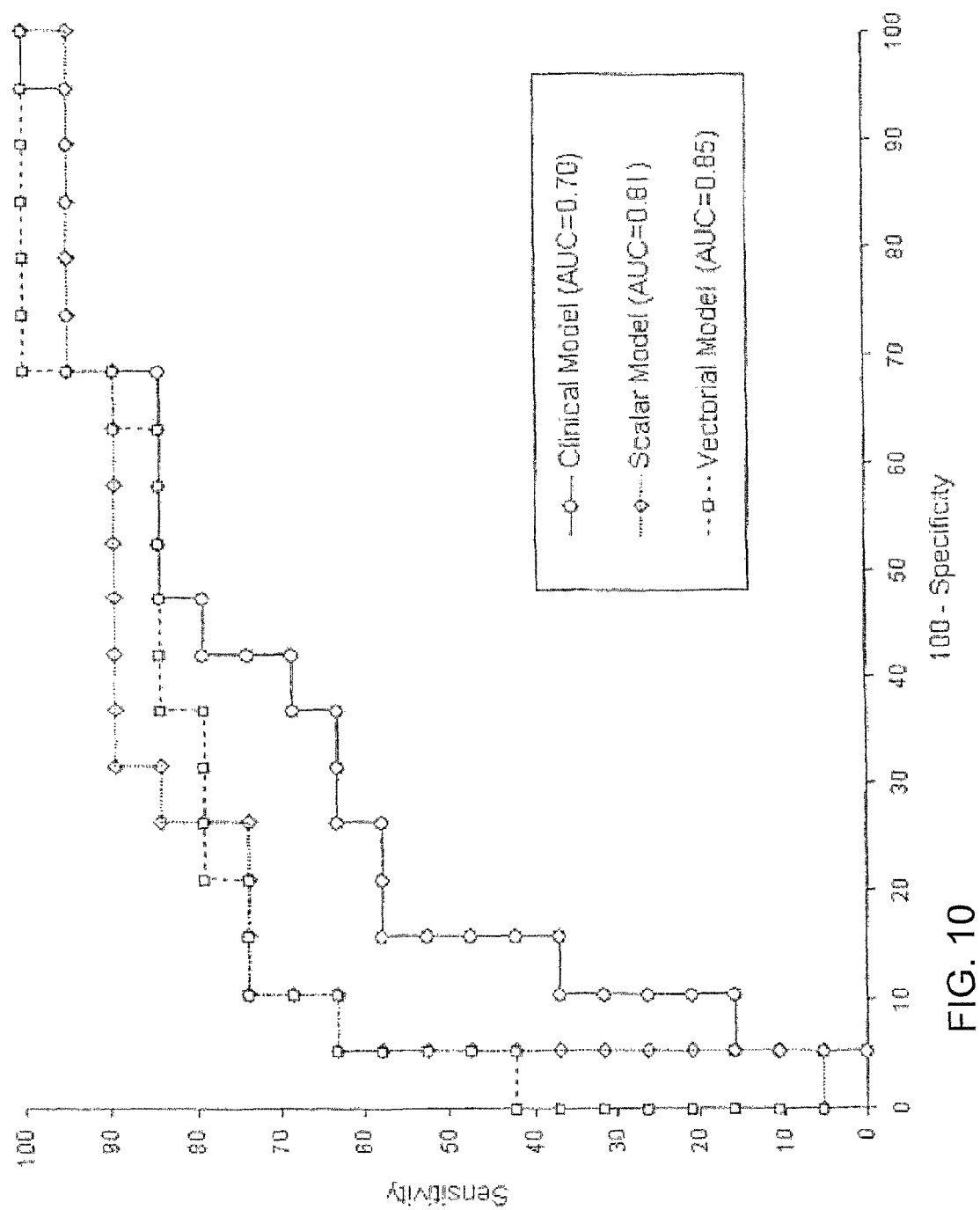
FIG. 10 illustrates one example of test results comparing clinical and scalar models for assessing repolarization abnormalities with one embodiment of a new vectorial model for assessing repolarization abnormalities.

FIG. 10 illustrates one example of test results comparing clinical and scalar models for assessing repolarization abnormalities with one embodiment of a new vectorial model for assessing repolarization abnormalities. This set of data gathers recordings from 40 individuals (18 females) in whom 4 recordings were acquired over a period of two days following a parallel-study design (2 recordings at specific hour of the day). The first day was baseline (2 recordings), and during the second day each individual received a dose of moxifloxacin (n=20) or a dose of placebo (n=20). The individuals had 1 recording acquired before dosing and one ECG acquired 2 hours after dosing. There were no differences in age between placebo and moxifloxacin groups: 28±7 vs. 26±8 yrs, respectively. Gender was evenly distributed in each group.

FIG. 10 illustrates ROC curves for the 3 models developed on 160 ECGs. The model using vectorial factors is the most discriminant one. The term "AUC"=area under the ROC curve.

Following the statistical strategy based on logistic regression models, we implemented 3 models: 1) a clinical model including (QT/QTc, RR. Age and gender), 2) a scalar model including the clinical factors and a set of measurements from lead 11 (see Table 2 below), and 3) a vectorial model considering the clinical factors in addition to a set of vectorial factors. The model selection was based on the best subset selection using the AIC criterion. The selected models are described in Table 2. The three models were compared using receiver operating characteristics (ROC) curves provided in FIG. 3. The factors selected in these models are given in Table 2.

TABLE 2 list of the parameters included in the best models based on the A(C criterion. All selected values have a p value <0.05 in their respective logistic models.

| | AUC | Factors |
|---|---|---|
| Clinical Model | 0.70 | QT |
| Clinical Model ($QT_c$) | 0.69 | $QT_c$ |
| Scalar Model | 0.81 | QTapex, Tmag |
| Vectorial Model | 0.85 | QT, $ERD_{30\%}$, $TRD_{30\%}$ |

One may note that RR interval is not selected in the model, this is explained by the fact that moxifloxacin does not affect heart rate. The use of Tmag. (magnitude of T-wave in lead II) and QTapex interval is associated with an approximately 11% increase of the area under the ROC curve (AUC). Using the vectorial parameters $TRD_{30\%}$ and $LRD_{30\%}$ is associated with a 15% improvement based on AUC. These novel parameters bring complementary information to QT prolongation when induced by a drug modifying the $I_{Kr}$ current in myocardial cells.

The advantages of a method and system for assessing repolarization abnormalities have been discussed herein. Embodiments discussed have been described by way of example in this specification. It will be apparent to those skilled in the art that the forgoing detailed disclosure is intended to be presented by way of example only, and is not limiting. Various alterations, improvements, and modifications will occur and are intended to those skilled in the art, though not expressly stated herein. These alterations, improvements, and modifications are intended to be suggested hereby, and are within the spirit and the scope of the claimed invention. Additionally, the recited order of processing elements or sequences, or the use of numbers, letters, or other designations therefore, is not intended to limit the claims to any order, except as may be specified in the claims. Accordingly, the invention is limited only by the following claims and equivalents thereto.

What is claimed is:

1. A method for assessing repolarization abnormalities, comprising:
   using a processor, identifying at least two repolarization signals from a set of electrocardiogram (ECG) signals;
   using the processor, performing principal component analysis on the at least two repolarization signals to extract at least eigenvectors $ev_1$ and $ev_2$;
   using the processor, determining a maximum vector MV based on a transformed ECG signal in a plane defined by $ev_1$ and $ev_2$; and
   using the processor, determining a repolarization duration which is based on the maximum vector MV.

2. The method of claim 1, further comprising: filtering the set of ECG signals.

3. The method of claim 2, wherein filtering the set of ECG signals comprises low-pass FIR filtering the ECG signals.

4. The method of claim 2, wherein filtering the set of ECG signals comprises removing a wandering baseline.

5. The method of claim 2, further comprising: detecting at least one QRS complex in the set of ECG signals.

6. The method of claim 5, wherein identifying at least two repolarization signals from the set of ECG signals comprises defining each of the at least two repolarization signals as starting from a point J and ending at a point relative to a following R peak.

7. The method of claim 6, wherein the point relative to the following R peak comprises a point which is an arbitrary point in time prior to the following R peak.

8. The method of claim 7, wherein the arbitrary point in time prior to the following R peak comprises a point which is approximately 220 milliseconds prior to the following R peak.

9. The method of claim 2, wherein filtering the set of ECG signals comprises statistically combining multiple beats from the ECG signals.

10. The method of claim 9, wherein statistically combining multiple beats from the ECG signals comprises creating a set of median beats, each median beat from one of the ECG signals.

11. The method of claim 2, wherein filtering the set of ECG signals comprises discarding one or more leading beats from the ECG signals.

12. The method of claim 2, wherein filtering the set of ECG signals comprises discarding one or more trailing beats from the ECG signals.

13. The method of claim 2, wherein filtering the set of ECG signals comprises discarding beats which do not have a corresponding stable heart rate.

14. The method of claim 13, wherein discarding beats which do not have a corresponding stable heart rate comprises discarding beats which have a heart rate that varies by more than a certain percentage in a previous arbitrary time frame.

15. The method of claim 14, wherein the certain percentage is ten percent and the arbitrary time frame is two minutes.

16. The method of claim 1, wherein principal component analysis on the at least two repolarization signals to extract at least eigenvectors $ev_1$ and $ev_2$ comprises:
   subtracting a mean from the at least two repolarization signals to produce a data set with a mean of zero;
   calculating a covariance matrix for the data set;
   calculating a set of eigenvectors and corresponding eigenvalues for the covariance matrix;
   determining that a first eigenvector from the set of eigenvectors with the largest corresponding eigenvalue is the eigenvector $ev_1$; and
   determining that a second eigenvector from the set of eigenvectors with the second-largest corresponding eigenvalue is the eigenvector $ev_2$.

17. The method of claim 1, wherein determining the maximum vector MV comprises determining $MV = \max\{\overrightarrow{VECG}(t) - \overrightarrow{VECG}(T_Q)\}$,
   where $\overrightarrow{VECG}(t) = \overrightarrow{ev_1}(t) + \overrightarrow{ev_2}(t)$, and $T_Q$ is a time coinciding with a beginning of the QRS complex.

18. The method of claim 17, wherein determining the repolarization duration which is based on the maximum vector MV comprises determining an early repolarization duration (ERD) at a threshold percentage x % of MV, such that:
   $ERD_{x\%} = T_{MV} - T_E$, where $T_E$ is a value for t where the following equation is fulfilled:
   $$\|VECG(t) - VECG(T_{MV}) = MV \cdot x\%\|, \text{ with } t < T_{MV}.$$

19. The method of claim 17, wherein determining the repolarization duration which is based on the maximum vector MV comprises determining a late repolarization duration (LRD) at a threshold percentage x % of MV, such that:
   $LRD_{x\%} = T_L - T_{MV}$, where $T_L$ is a value for t where the following equation is fulfilled:
   $$\|VECG(t) - VECG(T_{MV}) = MV \cdot x\%\|, \text{ with } t > T_{MV}.$$

20. The method of claim 17, wherein determining the repolarization duration which is based on the maximum vector MV comprises determining:
   a) an early repolarization duration (ERD) at a first threshold percentage x1% of MV, such that:
   $ERD_{x1\%} = T_{MV} - T_E$, where $T_E$ is a value for t where the following equation is fulfilled:
   $$\|VECG(t) - VECG(T_{MV}) = MV \cdot x1\%\|, \text{ with } t < T_{MV};$$
   b) a late repolarization duration (LRD) at a second threshold percentage x2% of MV, such that:
   $LRD_{x2\%} = T_L - T_{MV}$, where $T_L$ is a value for t where the following equation is fulfilled:
   $$\|VECG(t) - VECG(T_{MV}) = MV \cdot x2\%\|, \text{ with } t > T_{MV}; \text{ and}$$
   c) a total repolarization duration (TRD) such that $TRD = ERD_{x1\%} + LRD_{x2\%}$.

21. The method of claim 20, wherein the first threshold percentage x1% and the second threshold percentage x2% are equal.

22. The method of claim 20, wherein the first threshold percentage x1% and the second threshold percentage x2% are not equal.

23. The method of claim 1, further comprising:
constructing a T-loop based on a plot of a transformed ECG signal in a plane defined by $ev_1$ and $ev_2$.

24. The method of claim 23, wherein determining the maximum vector MV comprises determining a vector having a largest magnitude from a first sample point in the T-loop to a second sample point in the T-loop.

25. The method of claim 1, wherein determining the repolarization duration which is based on the maximum vector MV comprises:
taking a threshold percentage of a magnitude of MV to determine a threshold magnitude; and
projecting the threshold magnitude relative to an endpoint of MV to determine a beginning point and an ending point on the transformed ECG signal in the plane defined by $ev_1$ and $ev_2$.

26. The method of claim 25, wherein:
projecting the threshold magnitude around the endpoint of MV to determine the beginning point on the transformed ECG signal in the plane defined by $ev_1$ and $ev_2$ comprises determining the beginning point as a first sample point of the transformed ECG signal, the beginning point being a point which is closest to the projected threshold magnitude on a first side of the endpoint of MV; and
projecting the threshold magnitude around the endpoint of MV to determine the ending point on the transformed ECG signal in the plane defined by $ev_1$ and $ev_2$ comprises determining the ending point as a second sample point of the transformed ECG signal, the ending point being a point which is closest to the projected threshold magnitude on a second side of the endpoint of MV.

27. The method of claim 25, wherein:
projecting the threshold magnitude around the endpoint of MV to determine the beginning point on the transformed ECG signal in the plane defined by $ev_1$ and $ev_2$ comprises determining the beginning point as an interpolated beginning point between a first sample point and a second sample point of the transformed ECG signal on a first side of the endpoint of MV, the first and second sample points being the two closest points to the projected threshold magnitude on the first side of the endpoint of MV; and
projecting the threshold magnitude around the endpoint of MV to determine the ending point on the transformed ECG signal in the plane defined by $ev_1$ and $ev_2$ comprises determining the ending point as an interpolated ending point between a third sample point and a fourth sample point of the transformed ECG signal on a second side of the endpoint of MV, the third and fourth sample points being the two closest points to the projected threshold magnitude on the second side of the endpoint of MV.

28. The method of claim 25, wherein determining the repolarization duration which is based on the maximum vector MV comprises:
determining a beginning time corresponding to the beginning point;
determining a peak time corresponding to the endpoint of MV; and
determining an early repolarization duration (ERD) for the threshold percentage which comprises a time difference between the peak time and the beginning time.

29. The method of claim 28, wherein determining the repolarization duration which is based on the maximum vector MV further comprises:
determining an ending time corresponding to the ending point; and
determining a late repolarization duration (LRD) for the threshold percentage which comprises a time difference between the ending time and the peak time.

30. The method of claim 29, wherein determining the repolarization duration which is based on the maximum vector MV further comprises:
determining a total repolarization duration (TRD) for the threshold percentage comprising the sum of ERD and LRD.

31. The method of claim 1, wherein determining the repolarization duration which is based on the maximum vector MV comprises:
taking a threshold percentage of a magnitude of MV to determine a threshold magnitude; and
projecting the threshold magnitude relative to an endpoint of MV to determine a beginning point on the transformed ECG signal in the plane defined by $ev_1$ and $ev_2$.

32. The method of claim 31, wherein:
projecting the threshold magnitude around the endpoint of MV to determine the beginning point on the transformed ECG signal in the plane defined by $ev_1$ and $ev_2$ comprises determining the beginning point as a first sample point of the transformed ECG signal, the beginning point being a point which is closest to the projected threshold magnitude on a first side of the endpoint of MV.

33. The method of claim 31, wherein:
projecting the threshold magnitude around the endpoint of MV to determine the beginning point on the transformed ECG signal in the plane defined by $ev_1$ and $ev_2$ comprises determining the beginning point as an interpolated beginning point between a first sample point and a second sample point of the transformed ECG signal on a first side of the endpoint of MV, the first and second sample points being the two closest points to the projected threshold magnitude on the first side of the endpoint of MV.

34. The method of claim 31, wherein determining the repolarization duration which is based on the maximum vector MV comprises:
determining a beginning time corresponding to the beginning point;
determining a peak time corresponding to the endpoint of MV; and
determining an early repolarization duration (ERD) for the threshold percentage which comprises a time difference between the peak time and the beginning time.

35. The method of claim 1, wherein determining the repolarization duration which is based on the maximum vector MV comprises:
taking a threshold percentage of a magnitude of MV to determine a threshold magnitude; and
projecting the threshold magnitude relative to an endpoint of MV to determine an ending point on the transformed ECG signal in the plane defined by $ev_1$ and $ev_2$.

36. The method of claim 35, wherein:
projecting the threshold magnitude around the endpoint of MV to determine the ending point on the transformed ECG signal in the plane defined by $ev_1$ and $ev_2$ comprises determining the ending point as a sample point of the transformed ECG signal, the ending point being a point which is closest to the projected threshold magnitude on a second side of the endpoint of MV.

37. The method of claim 35, wherein:
projecting the threshold magnitude around the endpoint of MV to determine the ending point on the transformed ECG signal in the plane defined by $ev_1$ and $ev_2$ comprises determining the ending point as an interpolated ending point between a first sample point and a second sample point of the transformed ECG signal on a second side of the endpoint of MV, the first and second sample points being the two closest points to the projected threshold magnitude on the second side of the endpoint of MV.

38. The method of claim 37, wherein determining the repolarization duration which is based on the maximum vector MV further comprises:
determining a peak time corresponding to the endpoint of MV;
determining an ending time corresponding to the ending point; and
determining a late repolarization duration (LRD) for the threshold percentage which comprises a time difference between the ending time and the peak time.

39. The method of claim 1, wherein determining the repolarization duration which is based on the maximum vector MV comprises:
taking a first threshold percentage of a magnitude of MV to determine a first threshold magnitude;
taking a second threshold percentage of the magnitude of MV to determine a second threshold magnitude;
projecting the first threshold magnitude relative to an endpoint of MV to determine a beginning point on the transformed ECG signal in the plane defined by $ev_1$ and $ev_2$; and
projecting the second threshold magnitude relative to an endpoint of MV to determine an ending point on the transformed ECG signal in the plane defined by $ev_1$ and $ev_2$.

40. The method of claim 39, wherein:
projecting the first threshold magnitude around the endpoint of MV to determine the beginning point on the transformed ECG signal in the plane defined by $ev_1$ and $ev_2$ comprises determining the beginning point as a first sample point of the transformed ECG signal, the beginning point being a point which is closest to the projected first threshold magnitude on a first side of the endpoint of MV; and
projecting the second threshold magnitude around the endpoint of MV to determine the ending point on the transformed ECG signal in the plane defined by $ev_1$ and $ev_2$ comprises determining the ending point as a second sample point of the transformed ECG signal, the ending point being a point which is closest to the projected second threshold magnitude on a second side of the endpoint of MV.

41. The method of claim 39, wherein:
projecting the first threshold magnitude around the endpoint of MV to determine the beginning point on the transformed ECG signal in the plane defined by $ev_1$ and $ev_2$ comprises determining the beginning point as an interpolated beginning point between a first sample point and a second sample point of the transformed ECG signal on a first side of the endpoint of MV, the first and second sample points being the two closest points to the projected first threshold magnitude on the first side of the endpoint of MV; and
projecting the second threshold magnitude around the endpoint of MV to determine the ending point on the transformed ECG signal in the plane defined by $ev_1$ and $ev_2$ comprises determining the ending point as an interpolated ending point between a third sample point and a fourth sample point of the transformed ECG signal on a second side of the endpoint of MV, the third and fourth sample points being the two closest points to the projected second threshold magnitude on the second side of the endpoint of MV.

42. The method of claim 39, wherein determining the repolarization duration which is based on the maximum vector MV comprises:
determining a beginning time corresponding to the beginning point;
determining a peak time corresponding to the endpoint of MV; and
determining an early repolarization duration (ERD) for the first threshold percentage which comprises a time difference between the peak time and the beginning time.

43. The method of claim 42, wherein determining the repolarization duration which is based on the maximum vector MV further comprises:
determining an ending time corresponding to the ending point; and
determining a late repolarization duration (LRD) for the second threshold percentage which comprises a time difference between the ending time and the peak time.

44. The method of claim 43, wherein determining the repolarization duration which is based on the maximum vector MV further comprises:
determining a total repolarization duration (TRD) comprising the sum of ERD and LRD.

45. A computer readable medium having stored thereon instructions for assessing repolarization abnormalities, which, when executed by a processor, causes the processor to perform the steps according to claim 1.

46. A system for assessing repolarization abnormalities, comprising:
a processor configured to determine a repolarization duration which is based on a maximum vector MV from transformed ECG repolarization signals in a plane defined by eigenvectors $ev_1$ and $ev_2$ which result from principal component analysis on the ECG repolarization signals from ECG data;
a data input coupled to the processor and configured to provide the processor with the ECG data; and
a user interface coupled to either the processor or the data input.

47. The system of claim 46, wherein the processor is configured to be at least partially implantable in a subject's body.

48. The system of claim 46, further comprising a database coupled to the processor.

49. The system of claim 46, further comprising a database coupled to the data input.

50. The system of claim 46, further comprising an ECG capture device coupled to the data input.

51. The system of claim 50, wherein the ECG capture device is selected from the group consisting of a Holter monitor; a twelve-lead monitor; an 8 lead monitor; a monitor using a bipolar lead system, and a monitor using a unipolar lead system.

52. The system of claim 50, wherein the ECG capture device is coupled to the data input by a wireless connection.

53. The system of claim 52, wherein the ECG capture device is configured to transmit data to the data input during times which do not interfere with data measurement times of the ECG capture device.

54. The system of claim 50, wherein at least a portion of the ECG capture device is implantable in a subject's body.

55. The system of claim 54, further comprising a treatment device coupled to the processor, and wherein the processor is further configured to activate the treatment device to attempt to correct a repolarization abnormality indicated by the repolarization duration.

56. The system of claim 55, wherein the treatment device is implantable in the subject's body.

57. The system of claim 55, wherein the treatment device comprises a pharmacological agent administrator.

58. The system of claim 55, wherein the treatment device comprises a defibrillator.

59. The system of claim 46, wherein the processor and the data input are coupled together via a network.

60. The system of claim 46, further comprising:
an ECG capture device coupled to the data input; and
a pharmacological agent administrator coupled to the processor.

61. The system of claim 60, wherein the processor is further configured to:
administer a pharmacological agent with the pharmacological agent administrator;
capture a post-administration set of ECG signals; and
determine a post-administration repolarization duration based on at least two ECG signals in the post-administration set of ECG signals.

62. The system of claim 61, wherein the processor is further configured to:
prior to administering the pharmacological agent, capture a pre-administration set of ECG signals; and
determine a pre-administration repolarization duration based on at least two ECG signals in the pre-administration set of ECG signals.

63. The system of claim 62, wherein the processor is further configured to compare the pre-administration repolarization duration with the post-administration repolarization duration.

64. The system of claim 46, wherein the repolarization duration comprises an early repolarization duration (ERD) determined by:
taking a first threshold percentage of a magnitude of MV to determine a first threshold magnitude;
projecting the first threshold magnitude relative to an endpoint of MV to determine a beginning point on the transformed ECG signal prior to the endpoint of MV;
determining a beginning time corresponding to the beginning point;
determining a peak time corresponding to the end point of MV; and
determining the ERD for the first threshold percentage, the ERD comprising a time difference between the peak time and the beginning time.

65. The system of claim 64, wherein the repolarization duration also comprises a late repolarization duration (LRD) further determined by:
taking a second threshold percentage of the magnitude of MV to determine a second threshold magnitude;
projecting the second threshold magnitude relative to the endpoint of MV to determine an ending point on the transformed ECG signal after the endpoint of MV;
determining an ending time corresponding to the ending point; and
determining the LRD for the second threshold percentage, the LRD comprising a time difference between the ending time and the peak time.

66. The system of claim 65, wherein the repolarization duration further comprises a total repolarization duration (TRD) which comprises the sum of the ERD and the LRD.

67. The system of claim 65, wherein the first threshold percentage equals the second threshold percentage.

68. The system of claim 46, wherein the user interface is configured to display the ECG data.

69. The system of claim 46, wherein the user interface is configured to display a T-loop plotted in a preferential plane.

70. The system of claim 46, wherein the user interface is configured to display a primary component the ECG repolarization signals versus time.

71. The system of claim 46, wherein the user interface is configured to display a calculated parameter selected from the group consisting of ERD, LRD, and TRD, the calculated parameter being determined for at least one threshold percentage.

72. The system of claim 46, wherein the user interface is configured to allow a user to select the ECG data from a database.

73. The system of claim 46, wherein the user interface is configured to allow a user to start and stop collecting data from an ECG capture device.

74. A method for analyzing an effect of a pharmacological agent on heart repolarization, comprising:
obtaining a first set of ECG signals;
identifying at least two repolarization signals from the first set of ECG signals;
principal component analysis on the at least two repolarization signals from the first set of ECG signals to extract at least first eigenvectors $ev_{1-1}$ and $ev_{1-2}$;
determining a first maximum vector $MV_1$ based on a first transformed ECG signal in a first plane defined by $ev_{1-1}$ and $ev_{1-2}$;
determining a first repolarization duration which is based on the first maximum vector $MV_1$;
administering the pharmacological agent;
obtaining a second set of ECG signals;
identifying at least two repolarization signals from the second set of ECG signals;
principal component analysis on the at least two repolarization signals from the second set of ECG signals to extract at least second eigenvectors $ev_{2-1}$ and $ev_{2-2}$;
determining a second maximum vector $MV_2$ based on a second transformed ECG signal in a second plane defined by $ev_{2-1}$ and $ev_{2-2}$;
determining a second repolarization duration which is based on the second maximum vector $MV_2$; and
detecting a repolarization abnormality based on the first repolarization duration and the second repolarization duration.

75. A method for assessing repolarization abnormalities, comprising:
a) low-pass FIR filtering a set of at least two ECG signals;
b) discarding one or more leading beats from the ECG signals;
c) discarding one or more trailing beats from the ECG signals;
d) discarding beats from the ECG signals which have a heart rate that varies by more than ten percent in beats of the previous two minutes;
e) identifying at least two repolarization signals from the at least two ECG signals by defining each of the at least two repolarization signals as starting from a point J and ending at a point which is approximately 220 milliseconds prior to a following R peak;
f) principal component analysis on the at least two repolarization signals to extract at least eigenvectors $ev_1$ and $ev_2$, wherein the principal component analysis comprises:

1) subtracting a mean from the at least two repolarization signals to produce a data set with a mean of zero;
2) calculating a covariance matrix for the data set;
3) calculating a set of eigenvectors and corresponding eigenvalues for the covariance matrix;
4) determining that a first eigenvector from the set of eigenvectors with the largest corresponding eigenvalue is the eigenvector $ev_1$; and
5) determining that a second eigenvector from the set of eigenvectors with the second-largest corresponding eigenvalue is the eigenvector $ev_2$;

g) determining the maximum vector MV based on a transformed ECG signal in a plane defined by $ev_1$ and $ev_2$; such that $MV = \max\{\overrightarrow{VECG}(t) - \overrightarrow{VECG}(T_Q)\}$ where $\overrightarrow{VECG}(t) = \vec{ev}_1(t) + \vec{ev}_2(t)$ and $T_Q$ is a time coinciding with a beginning of QRS complex for the transformed ECG signal;

h) determining an early repolarization duration (ERD) which is based on the maximum vector MV at a threshold percentage x % of MV, such that:
$ERD_{x\%} = T_{MV} - T_E$, where $T_E$ is a value for t where the following equation is fulfilled:
$\|VECG(t) - VECG(T_{MV})\| = MV \cdot x\ \%$, with $t < T_{MV}$;

i) determining a late repolarization duration (LRD) which is based on the maximum vector MV at the threshold percentage x % of MV, such that:
$LRD_{x\%} = T_L - T_{MV}$, where $T_L$ is the value for t where the following equation is fulfilled:
$\|VECG(t) - VECG(T_{MV})\| = MV \cdot x\ \%$, with $t > T_{MV}$ and j) determining a total repolarization duration (TRD) which is based on the maximum vector MV at the threshold percentage x % of MV, such that:
$TRD_{x\%} = ERD_{x\%} + LRD_{x\%}$.

* * * * *